(12) United States Patent
Bouchard et al.

(10) Patent No.: US 11,122,986 B2
(45) Date of Patent: Sep. 21, 2021

(54) CONNECTED PLASTIC/TEXTILE SHEET

(71) Applicant: SAINT-GOBAIN ADFORS, Courbevoie (FR)

(72) Inventors: Jonas Bouchard, Paris (FR); François Blondeau, Meaux (FR); Mehmet Kasmer, Wattrelos (FR)

(73) Assignee: SAINT-GOBAIN ADFORS, Courbevoie (FR)

( * ) Notice: Subject to any disclaimer, the term of this patent is extended or adjusted under 35 U.S.C. 154(b) by 0 days.

(21) Appl. No.: 16/345,849

(22) PCT Filed: Oct. 24, 2017

(86) PCT No.: PCT/FR2017/052923
§ 371 (c)(1),
(2) Date: Apr. 29, 2019

(87) PCT Pub. No.: WO2018/078270
PCT Pub. Date: May 3, 2018

(65) Prior Publication Data
US 2019/0254555 A1 Aug. 22, 2019

(30) Foreign Application Priority Data

Oct. 27, 2016 (FR) ...................................... 1660455

(51) Int. Cl.
*A61B 5/0531* (2021.01)
*A61B 5/00* (2006.01)
*G01D 21/00* (2006.01)
*G01K 7/16* (2006.01)
*G01L 1/00* (2006.01)

(52) U.S. Cl.
CPC .......... *A61B 5/0531* (2013.01); *A61B 5/6804* (2013.01); *G01D 21/00* (2013.01); *G01K 7/16* (2013.01); *G01L 1/005* (2013.01); *A61B 2560/0468* (2013.01)

(58) Field of Classification Search
CPC ................ A61B 5/0531; A61B 5/6804; A61B 2560/0468; G01D 21/00; G01K 7/16; G01L 1/005
See application file for complete search history.

(56) References Cited

U.S. PATENT DOCUMENTS

| | | | |
|---|---|---|---|
| 4,400,684 A | 8/1983 | Kushida et al. | |
| 5,915,758 A * | 6/1999 | Alfiero | H01R 11/286 29/854 |
| 9,719,876 B2 * | 8/2017 | Reverdy | G01L 9/007 |
| 2006/0254366 A1 | 11/2006 | Williamson et al. | |
| 2008/0170982 A1 * | 7/2008 | Zhang | C01B 32/15 423/447.3 |
| 2017/0224280 A1 * | 8/2017 | Bozkurt | A61F 13/42 |
| 2018/0249767 A1 * | 9/2018 | Begriche | A61B 5/0492 |

FOREIGN PATENT DOCUMENTS

WO    WO 01/75778 A1    10/2001

OTHER PUBLICATIONS

International Search Report as issued in International Patent Application No. PCT/FR2017/052923, dated Jan. 18, 2018.

* cited by examiner

*Primary Examiner* — Akm Zakaria
(74) *Attorney, Agent, or Firm* — Pillsbury Winthrop Shaw Pittman LLP

(57) ABSTRACT

A sheet includes a carrier made of an electrically non-conductive material and at least one sensor wire associated with said carrier, wherein the wire reacts electrically to an exterior stress.

26 Claims, 5 Drawing Sheets

CONNECTED PLASTIC/TEXTILE SHEET

CROSS-REFERENCE TO RELATED APPLICATIONS

This application is the U.S. National Stage of PCT/FR2017/052923, filed Oct. 24, 2017, which in turn claims priority to French patent application number 1660455, filed Oct. 27, 2016. The content of these applications are incorporated herein by reference in their entireties.

The present invention relates to the field of smart coatings. Specifically, it is a question of a textile or of a technical plastic sheet that is connected and used to detect and locate areally mechanical stresses (anti-break-in system) or problems with water infiltration on or in substrates such as plasterboards, mortar, concrete, paving, bricks, wood, tiling, piping, insulating foam or wool, or even geotextiles.

PRIOR ART

A multitude of textile sensor technologies providing various natures of detection for very varied applications currently exist. Textile sensors form part of what are commonly called smart textiles. Smart textiles have conventionally been defined as textiles capable of detecting and reacting to environmental conditions and phenomena such as a mechanical force, a temperature change, a chemical reaction or an electrical stimulation.

It is for example known to employ an item of clothing using a connected textile to generate a control signal, for example in order to control an audio player. Such a connected fabric uses a linear sensor including electrically conductive textile fibres and insulating textile fibres. The sensor comprises at least two conductive elements containing electrically conductive textile fibres. The insulating textile fibres are arranged to separate the two electrically conductive elements in the absence of pressure applied to said sensor. During a pressure on said sensor, electrical conduction occurs between the two conductive elements, allowing the control signal to be generated.

A first drawback of existing textile-sensor solutions is that they are designed for relatively small areas (shoes, clothes, seats) by way of piezoresistive materials or for very large areas (roads, bridges, airports) via optical fibres.

A second drawback is that these solutions are not multifunctional. Specifically, each solution aims to detect only a single parameter at a time (water, mechanical stresses and/or even an increase in temperature).

SUMMARY OF THE INVENTION

The present invention therefore proposes to solve these drawbacks by providing a sheet or a textile that is connected, i.e. equipped with sensors, allowing a plurality of different parameters to be detected and capable of being used both over small areas and large areas.

For this purpose, the invention relates to a sheet comprising a carrier made of an electrically non-conductive material and at least one sensor wire associated with said carrier, characterized in that said sensor wire reacts electrically to an exterior stress.

This invention advantageously allows a sheet to be obtained on which a wire that detects, simply, stresses that are applied thereto is arranged. These stresses may be an elongation, a pressure, a torsion, an increase in temperature and the presence of radiation, gas or liquid.

According to one feature of the invention, the sensor wire comprises conductive components and insulating components that are intimately associated and arranged to allow conductive bridges to appear between the conductive components of said wire, characterized in that said wire is associated with the carrier so that at least one exterior stress applied to said carrier is directly transmitted to said sensor wire in order to provoke a variation in the number of conductive bridges and cause an electrical reaction.

This feature of the invention allows a sensor wire to be obtained that, in the absence of stresses, has a low conductivity, allowing, during a stress, a clearer and therefore more easily detectable variation in conductivity to be obtained. In addition, this allows a larger amplitude variation to be obtained, and hence the intensity of the stress to be better detected.

According to one feature of the invention, said wire includes at least one strand formed from a spun yarn of conductive fibres, which yarn is composed of intermixed insulating polymeric fibres and conductive metal fibres.

According to one feature of the invention, said wire includes a filament made from an insulating material filled with conductive particles.

According to one feature of the invention, said wire includes a plurality of filaments at least two of which are conductive, the rest being insulating filaments.

According to one feature of the invention, the carrier is made of a plastic material.

According to one feature of the invention, the carrier is a textile composed of textile filaments or wires that may be randomly arranged with respect to one other, the carrier possibly, where appropriate, being woven, nonwoven, knitted or tressed.

According to one feature of the invention, the carrier is composed of glass fibres.

According to one feature of the invention, the carrier is made of paper.

According to one feature of the invention, said wire includes a plurality of strands and preferably between two and five strands. This plurality of strands advantageously allows the solidity of the wire and its reliability to be improved.

According to one feature of the invention, the sheet comprises a single wire.

According to one feature of the invention, said wire has a shape comprising a plurality of rectilinear segments that are parallel to one another, each segment comprising two ends allowing it to be connected to the preceding and following segments by a curved segment.

According to one feature of the invention, the sheet comprises a plurality of wires. The advantage here is to have a plurality of independent wires and therefore an increased reliability in case of breakage of one of the wires.

According to one feature of the invention, each wire has a rectilinear shape.

According to one feature of the invention, said each wire has a shape comprising one two rectilinear segments that are parallel to each other and connected by a curved segment.

According to one feature of the invention, the plurality of wires extends in a single direction.

According to one feature of the invention, said the plurality of sensor wires extends in at least two secant directions that are preferably perpendicular, in order to form a mesh. This mesh allows the location of the appearance of the stress to be detected with greater precision.

These various features of the invention will possibly be combined with one another.

The invention furthermore relates to an assembly comprising a plurality of sheets according to the invention, characterized in that two adjacent sheets are connected in series.

The advantage here is to be able to produce sheets of standard size able to be connected together.

The invention also relates to a detecting device comprising the sheet or the assembly according to the invention, characterized in that it furthermore comprises a detecting circuit that is connected to said wire(s) in order to detect electrical reactions during mechanical stresses applied to said carrier(s) and transmitted directly to said wire(s).

According to one feature of the invention, said detecting device comprises one detecting circuit for connection to all of the sensor wires.

According to one feature of the invention, said detecting device comprises one detecting circuit for each wire.

The invention furthermore relates to a structure comprising a substrate on which the detecting device according to the invention is placed.

According to one feature of the invention, said substrate is chosen from the list comprising: plasterboard, mortar, concrete, brick, tiling, piping, insulating foam or wool, and wood.

The invention furthermore relates to a method for detecting an exterior stress on a detecting device, said method comprising the following steps:
 providing the detecting device;
 sending, sequentially or continuously, a current to the sensor wire via the detecting circuit;
 measuring an electrical parameter, preferably conductivity, and saving these measured values;
 processing these values in the detecting circuit to generate a signal representative of the electrical parameter.

DESCRIPTION OF THE FIGURES

Other particularities and advantages will become clearly apparent from the completely nonlimiting description that is given thereof below, by way of indication, and with reference to the appended drawings, in which.

DETAILED DESCRIPTION OF THE INVENTION

Figure 1:
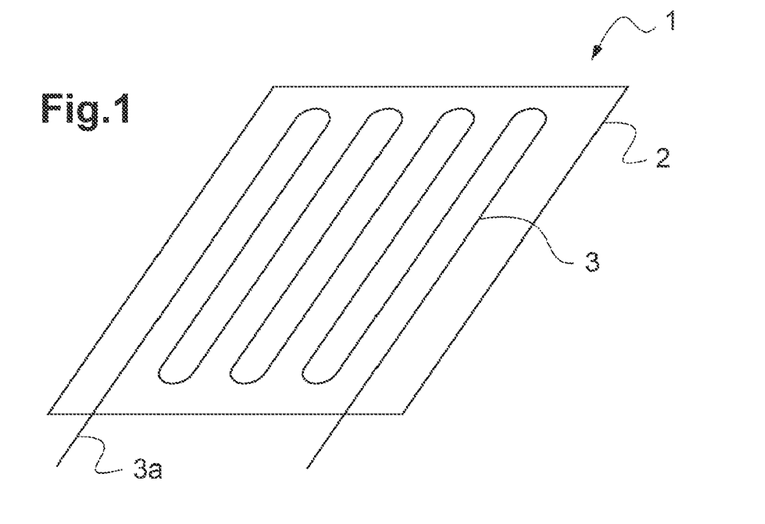
FIGS. 1 to 3 are schematic representations of the sheet and of the wire according to the invention.

FIG. 1 shows a connected sheet or strip according to the invention. Such a strip or sheet 1 is employed to be applied/fastened to substrates such as plasterboards, mortar, concrete, paving, bricks, wood, tiling, piping, insulating foam or wool, or even geotextiles. This sheet will possibly thus be arranged on the partitioning walls, exterior wall, ceiling or floor of a building. This connected sheet is used in applications such as anti-break-in systems, detection of infiltration problems or earthquake monitoring. It will also be possible for the sheet to be sufficient in itself.

This strip 1 comprises a carrier 2. This carrier 2 is chosen to be insulating, preferably flexible and may be a plastic film or a (glass fibre) textile or a piece of paper. A textile is considered to be an assembly of wires or filaments that may be randomly arranged with respect to one another. This textile may be woven, nonwoven, knitted or tressed. The carrier 2 is also chosen to be electrically non-conductive.

With this carrier 2 is associated at least one wire 3, also referred to as the sensor wire(s). This sensor wire comprises conductive and insulating components that are intimately associated and arranged to allow conductive bridges to appear between the conductive components.

Figure 2A:
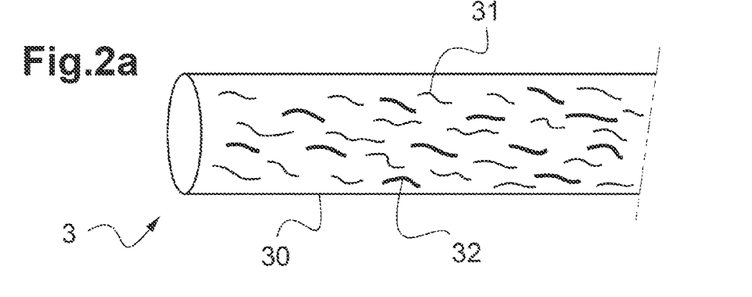

In a first embodiment shown in FIG. 2a, the sensor wire 3 is a strand 30 made up of a spun yarn of conductive fibres, which yarn is composed of insulating polymeric fibres 31 forming insulating components and conductive fibres 32 forming conductive components, which components are intermixed as shown in FIG. 2.

Figure 2B:
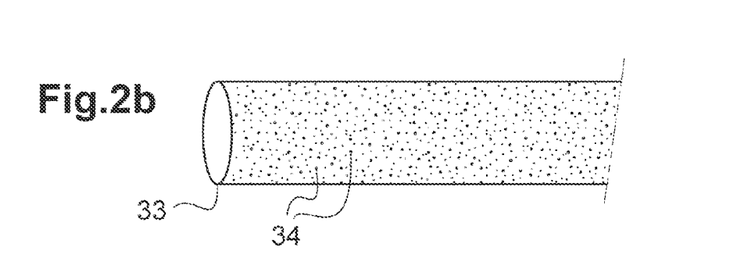

In a second embodiment shown in FIG. 2b, the sensor wire 3 is a single filament 33 made from an insulating material forming an insulating component filled with conductive particles 34 forming conductive components.

Figure 2C:
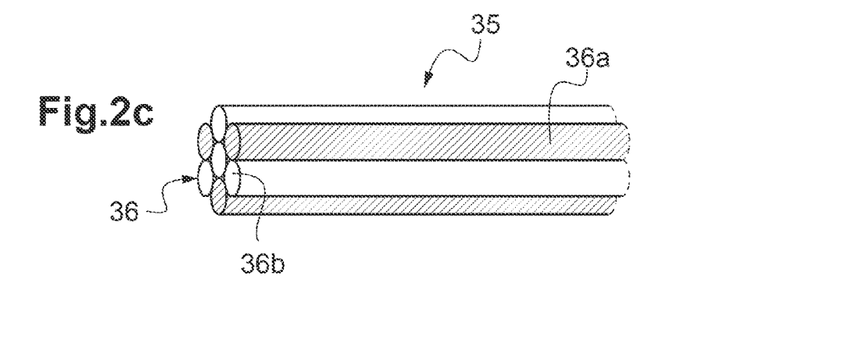

In a third embodiment shown in FIG. 2c, the sensor wire 3 is a strand 35 comprising a multitude of filaments 36. This multitude of filaments comprises conductive filaments 36a forming conductive components and insulating filaments 36b forming insulating components.

The fibres, filaments or conductive particles may be of stainless steel or of aluminium, of copper or of silver, of gold or of nickel, of carbon, carbon nanotubes, of carbon black, of graphite, of graphene, of organic conductive or semiconductor polymers such as polypyrrole, polyaniline, polythiophene, poly(p-phenylene sulphide), poly(p-phenylene vinylene), polyacetylenes, polyfluorenes, polypyrenes, polyazulenes, polynaphthalenes, metallized fibres and/or fibres with a conductive coating or a conductive size.

The insulating filaments or fibres 31 may also be of various types: polyester, polypropylene, polyethylene, polyamide, aramide, polylactic acid, polyvinyl alcohol, polyacrylate, glass, quartz, polybenzoxazole, polymethyl methacrylate, polytetrafluoroethylene, polyimide, polyetherimide, polyurethane, chlorofibre, elastane, cotton, wool, linen, hemp, jute, sisal, coir, bamboo, kenaf, ramie, silk, cellulose and/or viscose.

This sensor wire 3 is associated with the carrier 2, i.e. it makes contact with the carrier 2. The sensor wire 3 may be co-woven, co-knitted, or co-tressed with the textile carrier 2 at very specific tensions to obtain optimal detection sensitivities. This sensor wire 3 may also be coated onto and/or thermally, mechanically, chemically and/or hydraulically associated with the carrier 2 with or without a specific baking cycle.

Therefore, it will be understood that a stress applied to the carrier 2 is, advantageously, directly transmitted to said sensor wire 3, which reacts accordingly.

To allow an exterior stress on the surface of the carrier 2 to be detected, this wire 3 is arranged on the carrier 2 to extend in one or more directions, possibly the directions of the (length and width) dimensions of the carrier 2.

Such a sensor wire 3 operates as follows. The structure of the sensor wire 3 is discontinuous and has a high void content that allows it a certain freedom to vary in diameter without however changing the organization of the fibres. When a tensile force is applied along the axis of the sensor wire 3, a reversible decrease in the diameter of the sensor wire to a certain point is observed. This limit corresponds approximately to that of the elastic zone of the wire to which is added the elastic performance of the individual insulating filaments/fibres composing the sensor wire 3.

The amount of conductive particles/filaments/fibres 32 present within the sensor wire 3 is quite obviously a very important parameter as regards the conductivity of the sensor wire. Specifically, the conduction occurs by metal-like conduction, by hopping or by tunneling and this requires contact between the conductive materials or a certain proximity. Conduction in a conductive wire is therefore related to the number of points of contact or bridges between the conductive particles/filaments/fibres 32. The greater the mass content of the conductive particles/filaments/fibres 32 the greater the probability of creating a conductive bridge. In parallel, the number of conductive particles/filaments/fibres in the cross section increases with the increase in mass content. Thus, the mechanical detection mechanism is based on the relationship that exists between mechanical stimulation and the variation in the number of bridges between the conductive particles/filaments/fibres 32.

When the carrier 2 equipped with the sensor wire 3 undergoes a mechanical stress such as a stretch, a mechanical force appears and engenders geometric variations within the sensor wire 3. In the elastic regime, the effect of the variation in diameter is to bring the conductive fibres 32 closer together in the cross section. This seems to result in new conductive bridges being created between the conductive particles/filaments/fibres 32 or in existing bridges being accentuated, and is accompanied by a proportional increase in conductivity. It will therefore be understood that the increase in the number of conductive bridges occurs within the very interior of the sensor wire 3, the sensor wire in itself being all that is needed to detect a stress.

The fact that the sensor wire 3 is partially made of insulating materials allows, normally/at rest, electrical conductivity to be as low as possible. This low rest conductivity allows the variation in conductivity caused by the application of a stress to be made clearer, as the conductivity passes from a low value to a high value. In addition, this low rest conductivity allows a larger amplitude variation to be obtained than is possible if the sensor wire has a high rest conductivity. This large amplitude allows the intensity of the stress to be more easily detected.

When the stress applied to the sheet 1 according to the invention increases, the elastic regime transitions to the plastic regime. At the end of the elastic zone, the conductive particles/filaments/fibres slide over one another and align then get further apart from one another in the plastic zone. During the alignment, the probability of creating a continuous conductive network increases. Further increasing the stress leads to the gradual degradation of the sensor wire 3 until it breaks. The conductivity follows the same trend and gradually decreases until reaching a conductivity of zero.

Therefore, it is possible to determine, to some extent, the size of the shock. Specifically, if the detected conductivity variation consists, over time, of an increase in conductivity and then a decrease in conductivity to a zero value, then it may be deduced therefrom that the stress applied to the substrate was such that it caused breakage of said sensor wire 3.

Likewise, a conductivity detected to drop almost instantaneously to zero means that the stress experienced is due to a violent shock that cut right through the sensor wire 3.

Therefore, it will be understood that the sensor wire 3 has no need for intermediate elements to see its electrical conduction change following a stress on the carrier 2. In particular, there is no need for additional conductive elements arranged on the carrier 2 to change the electrical conduction of said sensor wire 3.

Figure 3:
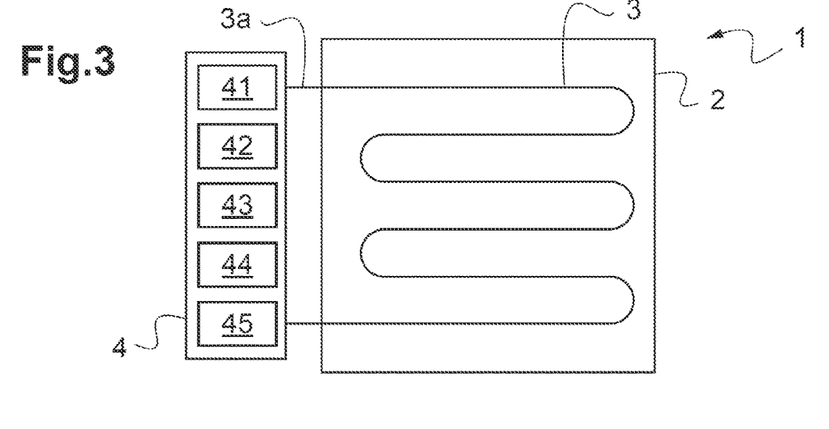

The two ends 3a of the sensor wire 3 of which connected to a detecting circuit 4 as may be seen in FIG. 3. This detecting circuit 4 is equipped with a detecting unit 41 for detecting variations in conductivity and delivering values representative of conductivity, with a processing unit 42 for processing the values representative of conductivity and delivering a representative signal, with a memory 43 for storing the values representative of conductivity and with a communication circuit 44 for transmitting the representative signal over a wired or wireless link, all thereof being supplied with power by a supply unit 45 that is either stand-alone or plugged into the mains. The detecting circuit 4 is then designed to send a current to the wire and measure an electrical parameter such as conductivity or resistivity. The measured values are saved and processed so that a signal representative of the measured parameter is generated.

According to the invention, the sensor wire 3 may be used to detect other parameters.

A second parameter detected by the connected sheet/strip 1 according to the invention is moisture. Specifically, any water that penetrates into the sensor wire 3 creates bridges between the conductive fibres, thereby enabling a significant increase in electrical conductivity. It becomes possible to detect this parameter with the same sensor wire 3 used to detect tensile stress.

A third possible detectable parameter is temperature. Specifically, according to the Nernst-Einstein equation, which allows conductivity to be calculated as a function of other fundamental parameters of the material:

$$\sigma = \frac{DZ^2 e^2 C}{k_B T}$$

where:
D is the diffusion coefficient of the charged species in question;
Z is the number of charges carried by the species;
e is the elementary charge, i.e. $1.602 \times 10^{-19}$ C;
C is the molar concentration of the species;
kB is Boltzmann's constant, i.e. about $1.3806 \times 10^{-23}$ J·K$^{-1}$; and
T is absolute temperature, expressed in kelvin.

It may therefore be seen that this conductivity depends on temperature and decreases as temperature increases. It thus becomes possible to determine a temperature variation undergone by the sheet 1.

To detect a stress such as an elongation, a pressure, a torsion, an increase in temperature or the presence of radiation, gas or liquid in the carrier 2, provision is made for a plurality of modes of execution.

In a first mode of execution shown in FIG. 3, a single sensor wire 3 is arranged on the carrier 2. In this case, the sensor wire 3 comprises a plurality of rectilinear or substantially rectilinear segments that are parallel to one another, two segments that are parallel with respect to each other being connected by a curved segment in order that all the segments form a single continuous sensor wire 3. This mode of execution allows, with a single sensor wire 3, a stress such as a stretch or the presence of moisture to be detected with a single sensor wire 3 over a large area.

In this first mode of execution, the detecting unit 4 therefore comprises two connecting terminals for the connection of the two ends 3a of the sensor wire 3.

In a second mode of execution, a plurality of sensor wires 3 are arranged on the carrier 2.

Figure 4:
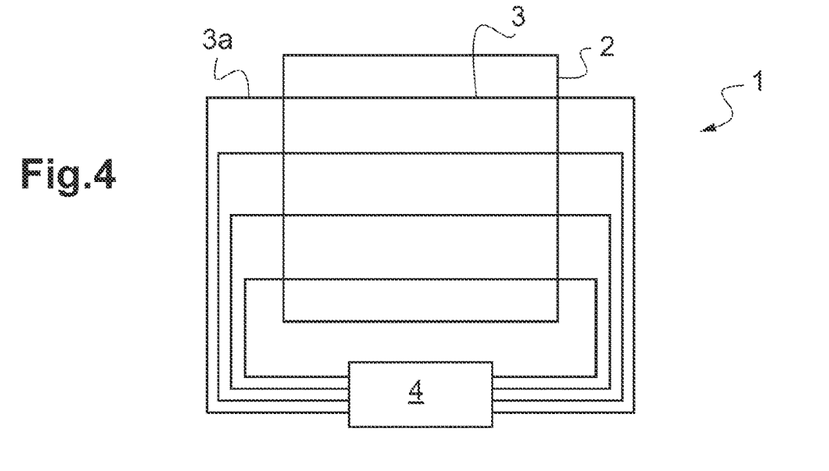
FIGS. 4 to 10 are schematic representations of modes of execution of the invention and of their variants.
Figure 5:
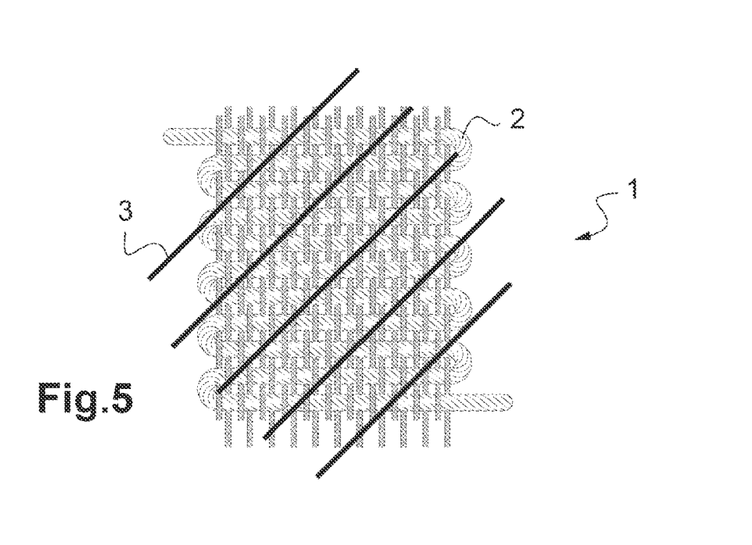

According to a first solution to this mode of execution, shown in FIG. 4, the wires 3 are placed on the carrier 2 so that each sensor wire 3 extends linearly in one direction, said sensor wires 3 being parallel to one another. This direction may be parallel to the direction of one of the dimensions of the carrier 2 or shifted angularly as shown in FIG. 5.

Figure 6:
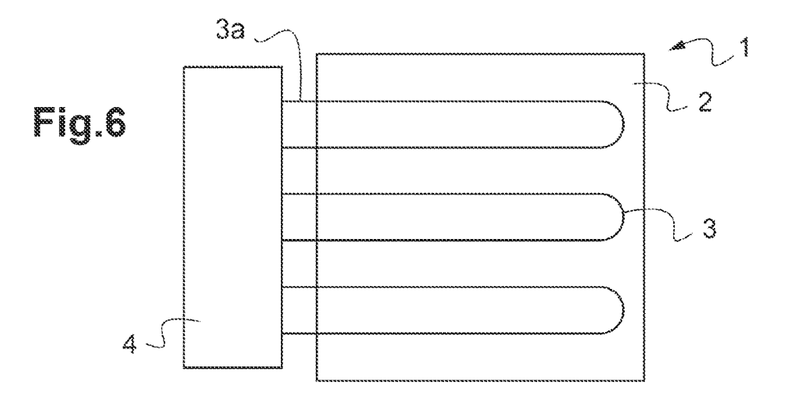

According to a second solution to this mode of execution, shown in FIG. 6, the sensor wires 3 are placed on the carrier 2 so that each sensor wire 3 has a shape composed of two rectilinear or substantially rectilinear segments that are parallel and connected by a curved segment. The sensor wires 3 are then arranged parallelly with respect to one another.

This second mode of execution allows a stress such as a stretch or the presence of moisture to be detected over a large area with higher precision. Specifically, as the carrier 2 is equipped with a plurality of sensor wires 3 that are independent from one another, the presence of a stress or moisture at a given point does not cause a variation in electrical conduction in each of the wires 3.

Moreover, having a plurality of sensor wires 3 allows reliability to be increased since cutting one sensor wire 3 does not stop the entirety of the carrier from being able to detect, as in the first mode of execution.

Lastly, as detection sensitivity is partially dependent on the length of the sensor wire 3, the second mode of execution makes it possible to obtain a detecting circuit 4 with a lower sensitivity but that nonetheless detects just as well.

In this case here, there may be one detecting circuit 4 per sensor wire 3 or just one detecting circuit 4 for all the sensor wires 3, as shown in FIG. 4.

In the first mode of execution and the second mode of execution, the one or more sensor wires 3 will be arranged on the carrier 2 in order to allow a detection coverage of at least 60% of the area of the carrier 2, preferably 75% and even more preferably 90% of the area of said carrier.

In one variant of the second mode of execution, the various sensor wires 3 are arranged to obtain an enhanced detection precision. To do this, the sensor wires 3 are arranged to form a mesh.

Figure 7:
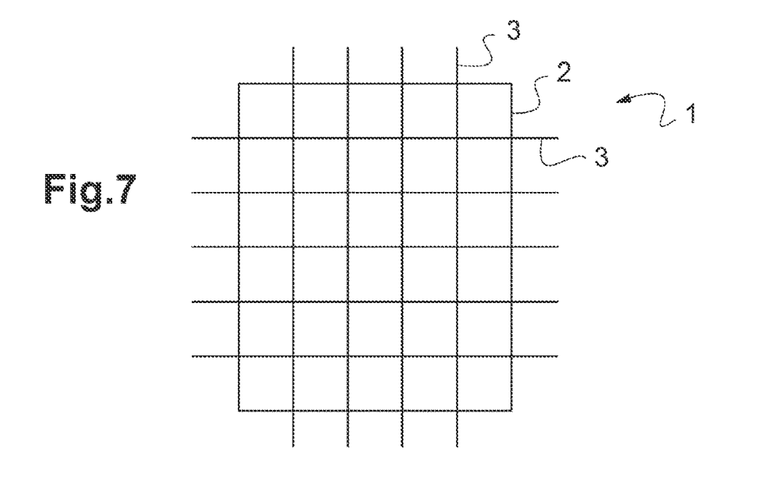

In the case of the first solution of said second mode of execution, shown in FIG. 7, the carrier 2 is equipped with a plurality of series of sensor wires 3. A first series comprises rectilinear sensor wires 3 that are parallel to one another and placed to extend in a first direction. A second series comprises rectilinear sensor wires 3 that are parallel to one another and placed to extend in a second direction, the first direction and the second direction being different. The sensor wires 3 of the first series and the sensor wires 3 of the second series being arranged on the carrier 2 so as to not make electrical contact. Together, the two series form a grid allowing the location at which the detected stress is located to be determined with precision.

Figure 8:
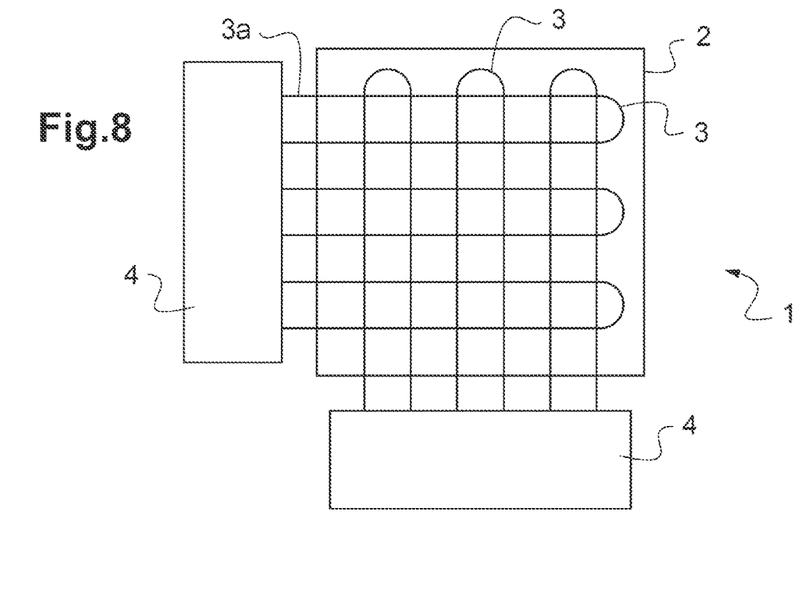

In the case of the second solution of said second mode of execution, shown in FIG. 8, the arrangement is performed in a similar way to that of the first solution. A first series comprises rectilinear sensor wires 3 that are parallel to one another and placed to extend in a first direction. A second series comprises rectilinear sensor wires 3 that are parallel to one another and placed to extend in a second direction, the first direction and the second direction being different. Each sensor wire 3 has a shape composed of two rectilinear segments that are parallel and connected by a curved segment.

Figure 9:
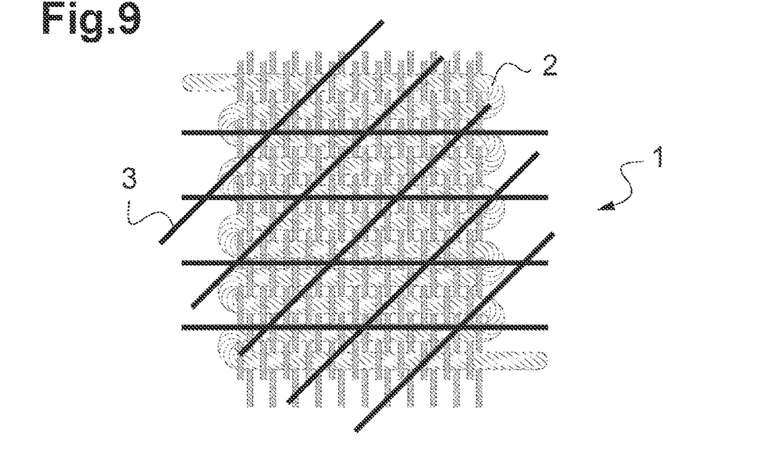
Figure 10:
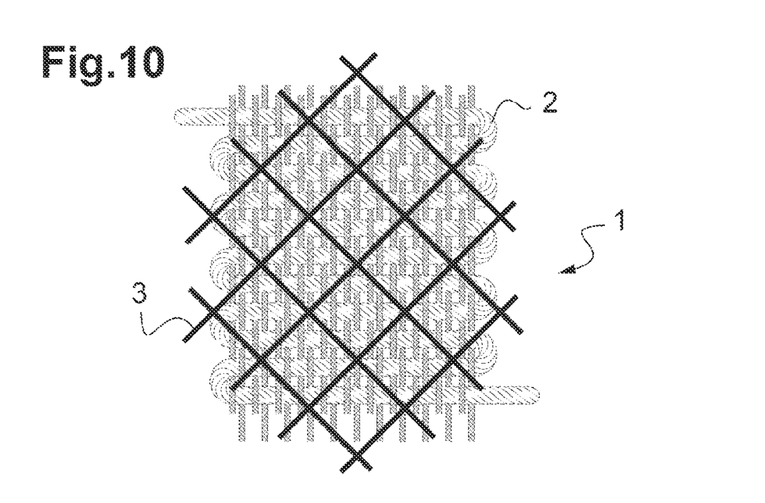

For this variant of the second mode of execution, the first direction and the second direction may be perpendicular or be secant with an angle preferably of 45°. The first direction and the second direction may be also be parallel to the length/width of the carrier or be angularly shifted with respect to the directions of these dimensions as may be seen in FIGS. 9 and 10. This angle will possibly be chosen depending on the shape of the substrate. Specifically, the area of the substrate over which the connected sheet/strip 1 is placed will possibly not be flat.

In this variant of the second mode of execution, provision will possibly be made for there to be one detecting circuit 4 per wire 3 or even one detecting circuit 4 per series of wires 3 or indeed just one detecting circuit 4 for all the wires 3.

Figure 11:
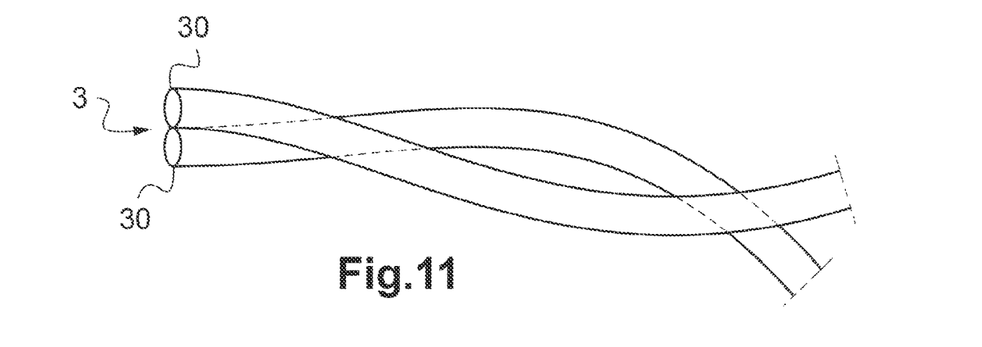
FIG. 11 is a schematic representation of a variant of the wire used in the sheet according to the invention.

In one variant of the invention, as shown in FIG. 11, the sensor wire 3 comprises a plurality of strands 30. Each strand 30 consists of a spun yarn of conductive fibres, said yarn being composed of intermixed insulating polymeric fibres 31 and conductive metal fibres 32. These various strands 30 are twisted in order to form a single sensor wire 3. The sensor wire 3 will possibly comprise a number of strands 30 ranging from 2 to 5.

Multiplying the number of strands 30 firstly makes it possible to obtain a sensor wire 3 that is stronger, and also more reliable because accidental complete or partial breakage of one of the strands no longer disrupts the operation of the system.

In addition, this reinforcement of the wire 3 has an impact on the reinforcement of the carrier 2 or even of the carrier substrate. As the multistrand wire 3 is arranged directly on the carrier 2, it contributes to its mechanical reinforcement. In the same way, the mechanical reinforcement of the carrier 2 has an impact on the substrate that bears all the other elements.

Figure 12:
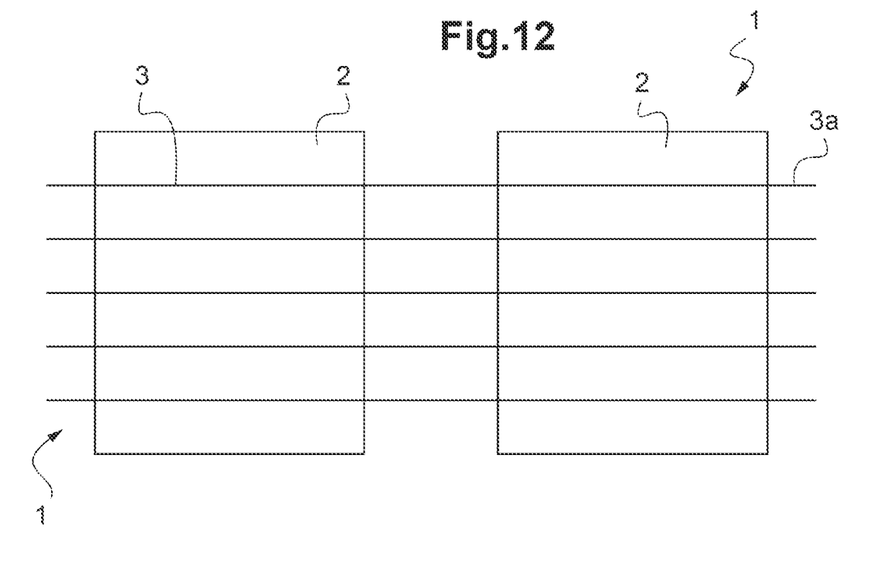
FIGS. 12 and 13 are schematic representations of a connection of a plurality of sheets according to the invention.
Figure 13:
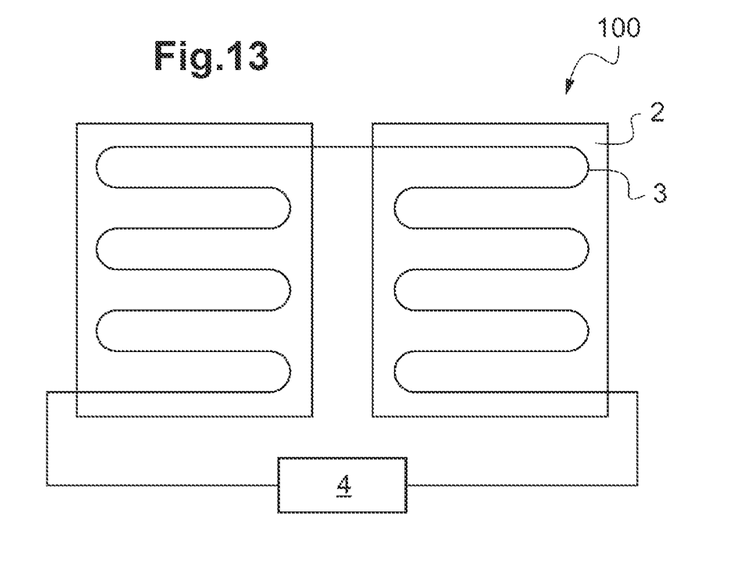

In one variant of the invention, shown in FIGS. 12 and 13, provision will possibly be made for a series of carriers 2 to be connectable to one another in series to form an assembly 100. To do this, the two free ends of the one or more wires 3 of each carrier 2, i.e. the ends for connection to the detecting circuit 4, are used. A first end of a sensor wire 3 of the first carrier 2 is connected to the detecting circuit 4 whereas the second end of said sensor wire 3 is connected to the first end of a sensor wire 3 of the second carrier 2 and so on. The second end of the sensor wire 3 of the last carrier 2 of the series is connected to the detecting circuit 4.

This variant is also applicable to carriers 2 with which a plurality of sensor wires 3 are associated. In this case, each sensor wire 3 of the carrier 2 is connected to a sensor wire 3 of the preceding and/or following carrier 2. Preferably, the carriers 2 are configured in the same way, i.e. the sensor wires 3 of these carriers 2 have the same layout. In this respect, the sensor wire 3 of a carrier 2 is connected in series with the sensor wire 3 of the following and/or preceding carrier, which has the same layout, allowing the series connection of the various carriers 2 to be simplified.

In this variant, provision will possibly be made for one detecting circuit 4 per sensor wire 3 or even one detecting circuit 4 per series of sensor wires 3 or indeed just one detecting circuit 4 for all the sensor wires 3.

Of course, the present invention is not limited to the illustrated example and various variants and modifications will be obvious to those skilled in the art.

For example, provision will possibly be made for the carrier on which the sensor wire 3 is arranged to be rigid, such as for example a carrier made of glass. This would allow a window or glazed door to be equipped in order to obtain an anti-break-in device, or even a temperature-regulating device using the variation in electrical conductivity of the wire as a function of the exterior temperature sensed by the wire of the glazing to control a heating/air-conditioning device.

In addition, it will be possible for a carrier 2 to comprise a rectilinear sensor wire 3 and a sensor wire 3 composed of two parallel rectilinear segments connected by a curved segment.

The invention claimed is:

1. A sheet comprising a carrier made of an electrically non-conductive material and at least one sensor wire associated with said carrier, wherein said at least one sensor wire has an electrical conductivity that varies upon application of an exterior stress to said at least one sensor wire, wherein said at least one sensor wire comprises insulating components and conductive components that are intimately associated to form said at least one sensor wire, said insulating components and conductive components being arranged within said at least one sensor wire to allow conductive bridges to appear between said conductive components of said at least one sensor wire, and wherein said at least one sensor wire is associated with the carrier so that at least one exterior stress applied to said carrier is directly transmitted to said at least one sensor wire in order to provoke a variation in the number of conductive bridges and cause a variation of the electrical conductivity of said at least one sensor wire.

2. The sheet according to claim 1, wherein said at least one sensor wire includes at least one strand formed from a spun yarn of conductive fibres, which yarn is composed of intermixed insulating fibres and conductive fibres.

3. The sheet according to claim 1, wherein said at least one sensor wire includes a filament made from an insulating material filled with conductive particles.

4. The sheet according to claim 1, wherein said at least one sensor wire includes a plurality of filaments at least two of which are conductive, the rest being insulating filaments.

5. The sheet according to claim 1, wherein the carrier is made of a plastic material.

6. The sheet according to claim 1, wherein the carrier is composed of textile filaments or wires that may be randomly arranged with respect to one other, the carrier being woven, nonwoven, knitted or tressed.

7. The sheet according to claim 6, wherein the carrier is composed of glass fibres.

8. The sheet according to claim 1, wherein the carrier is made of paper.

9. The sheet according to claim 1, wherein said at least one sensor wire includes a plurality of strands.

10. The sheet according to claim 1, comprising a single sensor wire.

11. The sheet according to claim 10, wherein said sensor wire has a shape comprising a plurality of rectilinear segments that are parallel to one another, each segment comprising two ends allowing it to be connected to the preceding and following segments by a curved segment.

12. The sheet according to claim 1, comprising a plurality of sensor wires.

13. The sheet according to claim 12, wherein each sensor wire has a rectilinear shape.

14. The sheet according to claim 12, wherein said each sensor wire has a shape comprising two rectilinear segments that are parallel to each other and connected by a curved segment.

15. The sheet according to claim 12, wherein the plurality of wires extends in a single direction.

16. The sheet according to claim 12, wherein the plurality of sensor wires extends in at least two secant directions, in order to form a mesh.

17. An assembly comprising a plurality of sheets according to claim 1, wherein two adjacent sheets are connected in series.

18. A detecting device comprising the sheet according to claim 1, and a detecting circuit that is connected to said at least one sensor wire in order to detect electrical reactions during mechanical stresses applied to said carrier and transmitted directly to said at least one sensor wire.

19. The detecting device according to claim 18, comprising a plurality of said sensor wires and said detecting circuit is connected to all of the sensor wires.

20. The detecting device according to claim 18, wherein said detecting circuit is connected to only one of said at least one sensor wire.

21. A structure comprising a substrate on which the detecting device according to claim 18 is placed.

22. The structure according to claim 21, wherein said substrate is chosen from the list comprising: plasterboard, mortar, concrete, brick, tiling, piping, insulating foam or wool, and wood.

23. A method for detecting an exterior stress on a detecting device according to claim 18, said method comprising:
providing the detecting device;
sending, sequentially or continuously, a current to the sensor wire via the detecting circuit;
measuring an electrical parameter and saving measured values;
processing the measured values in the detecting circuit to generate a signal representative of the electrical parameter.

24. The sheet according to claim 9, wherein said at least one sensor wire includes between two and five strands.

25. The sheet according to claim 16, wherein the at least two secant directions are perpendicular.

26. The method according to claim 23, wherein the electrical parameter is conductivity.

* * * * *